US012576006B2

(12) United States Patent
Gagne

(10) Patent No.: US 12,576,006 B2
(45) Date of Patent: Mar. 17, 2026

(54) SYSTEMS AND METHODS FOR THE PREPARATION OF FLUIDS FOR BIOPROCESS AND PHARMACEUTICAL APPLICATIONS

(71) Applicant: ALPHINITY USA, INC., Carson City, NV (US)

(72) Inventor: Michael C. Gagne, Carson City, NV (US)

(73) Assignee: ALPHINITY USA, INC., Carson City, NV (US)

( * ) Notice: Subject to any disclaimer, the term of this patent is extended or adjusted under 35 U.S.C. 154(b) by 277 days.

(21) Appl. No.: 18/245,839

(22) PCT Filed: Sep. 21, 2021

(86) PCT No.: PCT/US2021/051374
§ 371 (c)(1),
(2) Date: Mar. 17, 2023

(87) PCT Pub. No.: WO2022/066668
PCT Pub. Date: Mar. 31, 2022

(65) Prior Publication Data
US 2024/0033179 A1 Feb. 1, 2024

Related U.S. Application Data

(60) Provisional application No. 63/081,737, filed on Sep. 22, 2020.

(51) Int. Cl.
*A61J 1/10* (2006.01)
*A61J 1/22* (2006.01)
*C12M 1/00* (2006.01)

(52) U.S. Cl.
CPC . *A61J 1/10* (2013.01); *A61J 1/22* (2013.01); *C12M 23/14* (2013.01); *C12M 23/26* (2013.01); *C12M 23/40* (2013.01)

(58) Field of Classification Search
CPC .... A61J 1/10; A61J 1/1462; A61J 1/16; A61J 1/20; A61J 1/22; C12M 23/14; C12M 23/26; C12M 23/40; C12M 99/00
See application file for complete search history.

(56) References Cited

U.S. PATENT DOCUMENTS 4,282,863 A 8/1981 Beigler et al.
4,465,488 A 8/1984 Richmond et al.
(Continued)

FOREIGN PATENT DOCUMENTS

JP 58-115236 8/1983
JP H10-218252 A 8/1998
(Continued)

OTHER PUBLICATIONS

PCT International Preliminary Report on Patentability (Chapter I of the Patent Cooperation Treaty) for PCT/US2021/051374, Applicant: Alphinity USA, Inc., Form PCT/IB/326 and 373, dated Apr. 6, 2023 (11 pages).
(Continued)

*Primary Examiner* — Kai H Weng
(74) *Attorney, Agent, or Firm* — VISTA IP LAW GROUP LLP

(57) ABSTRACT

A system for the preparation of fluids for bioprocess and pharmaceutical applications uses one or more flexible bags that are pre-loaded with solid tablets contained therein of various buffer/media/physiological fluid constituents. Examples include salts, acids, bases, preservatives, proteins, amino acids, growth factors, small molecules, and drugs. The flexible bag contains one or more sealed or sealable openings that are used to add water to the interior of the flexible bag as well as remove fluid from the flexible bag. The one or more sealed openings may also be used as an outlet to remove fluid (e.g., buffer) from the flexible bag. The flexible bag may be stored in a deflated state aiding in (Continued)

the storage and/or transport of the flexible bag. Multiple flexible bags may be coupled to a manifold with valves to selectively fill and empty the flexible bags.

11 Claims, 6 Drawing Sheets

(56) References Cited

U.S. PATENT DOCUMENTS

| | | | |
|---|---|---|---|
| 4,467,588 A | 8/1984 | Carveth | |
| 4,484,920 A | 11/1984 | Kaufman et al. | |
| 4,602,910 A | 7/1986 | Larkin | |
| 5,484,431 A | 1/1996 | Scharf et al. | |
| 5,557,362 A | 9/1996 | Ueda | |
| 7,244,247 B1 | 7/2007 | Falciani et al. | |
| 10,465,157 B2 * | 11/2019 | Zhang | C12M 37/02 |
| 2005/0009697 A1 | 1/2005 | Ingelbrecht et al. | |
| 2006/0024045 A1 | 2/2006 | Yamamoto | |
| 2009/0219780 A1 | 9/2009 | Castillo et al. | |
| 2011/0003971 A1 | 1/2011 | Strittmatter et al. | |
| 2014/0137519 A1 * | 5/2014 | Goodwin | B65B 51/02 |
| | | | 141/10 |
| 2015/0059288 A1 | 3/2015 | Wu | |
| 2017/0023236 A1 | 1/2017 | Hardgrave | |
| 2017/0033583 A1 | 2/2017 | Inskeep | |
| 2017/0037362 A1 | 2/2017 | Neubauer et al. | |
| 2018/0252326 A1 | 9/2018 | Gagne et al. | |

FOREIGN PATENT DOCUMENTS

| | | |
|---|---|---|
| JP | 2005-512616 A | 5/2005 |
| JP | 2007-526106 | 9/2007 |
| JP | 2014-521405 A | 8/2014 |
| JP | 2018-537113 A | 12/2018 |
| WO | WO 1997/031692 A1 | 9/1997 |
| WO | WO 2000/023036 A1 | 4/2000 |
| WO | WO 03/035146 A1 | 5/2003 |
| WO | WO 2004/108262 A2 | 12/2004 |
| WO | WO 2005/025482 A1 | 3/2005 |
| WO | WO 2007/067882 A2 | 6/2007 |
| WO | WO 2010/132435 A1 | 11/2010 |
| WO | WO 2013/009765 A2 | 1/2013 |
| WO | WO 2017/106783 A1 | 6/2017 |
| WO | WO2017/038959 A1 | 3/2019 |
| WO | WO 2021/158448 A1 | 8/2021 |

OTHER PUBLICATIONS

The extended European search report dated Feb. 14, 2024 for European Patent Application No. 21873294.9, Applicant: Alphinity USA, Inc., (9 pages).

Response to the extended European search report dated Sep. 3, 2024 for European Patent Application No. 21873294.9, Applicant: Alphinity USA, Inc., (17 pages).

PCT International Search Report for PCT/US2021/051374, Applicant: Alphinity USA, Inc., Form PCT/ISA/210 and 220, dated Feb. 14, 2022 (5 pages).

PCT Written Opinion of the International Search Authority for PCT/US2021/051374, Applicant: Alphinity USA, Inc., Form PCT/ISA/237, dated Feb. 14, 2022 (9 pages).

Ready-to-use fluid management for inline conditioning (IC) large-scale chromatography systems, GE Healthcare Life Sciences, Aug. 2012, Application note 29-0257-24 AA, (4 pages).

Automated in-line buffer preparation from ready-made stock solutions in a mAB process step, GE Healthcare, Application note, 29260552 AA, Jun. 2017, (8 pages).

Michael Li et al., Process Analytical Technology-Based In-Line Buffer Dilution In Downstream Bioprocessing, Pharmaceutical Technology, Oct. 1, 2010, (8 pages).

Response to First Office Action dated Oct. 20, 2025 for Japanese Patent Application No. 2023-517861, (12 pages), English Translations for the Amended Claims only.

Response to Notice of Preliminary of Rejection dated Sep. 5, 2025 for Korean Patent Application No. 10-2023-7013170, (14 pages).

First Office Action dated Jul. 15, 2025 for Japanese Patent Application No. 2023-517861, (19 pages).

Notice of Preliminary of Rejection dated Jul. 7, 2025 for Korean Patent Application No. 10-2023-7013170, (4 pages).

First Examination Report dated Nov. 11, 2025 for European Patent Application No. 21873294.9, (4 pages).

\* cited by examiner

| Buffer A | Recipe |
|----------|--------|
| Tablet Type | # |
| #1 | 3 |
| #2 | 4 |
| #3 | 1 |

SYSTEMS AND METHODS FOR THE PREPARATION OF FLUIDS FOR BIOPROCESS AND PHARMACEUTICAL APPLICATIONS

RELATED APPLICATION

This Application is a U.S. National Stage filing under 35 U.S.C. § 371 of International Application No. PCT/US2021/051374, filed on Sep. 21, 2021, which claims priority to U.S. Provisional Patent Application No. 63/081,737 filed on Sep. 22, 2020, which are hereby incorporated by reference. Priority is claimed pursuant to 35 U.S.C. §§ 119, 371 and any other applicable statute.

TECHNICAL FIELD

The technical field generally relates to systems and methods for the preparation of fluids for bioprocess and pharmaceutical applications. In particular, the technical field relates to the use of flexible containers (e.g., flexible bags) that are pre-loaded with solid tablets or the like. The flexible containers are filled with water to dissolve the solid tablets and create a solution having a known concentration. Large volumes of fluids may be easily created having the desired concentrations.

BACKGROUND

Buffers and solutions contained buffers are needed in many applications. For example, buffer solutions are used in many pharmaceutical and biopharmaceutical operations. Buffer solutions are used in the preparation of drugs and other pharmaceuticals. For example, buffer solutions may be used in various wash, capture, and elution operations. Buffer solutions are also used as part of growth or maintenance media to maintain cells or other living organisms used in bioprocess operations. Physiological solutions also often buffered or contain buffered solutions. Ringer's lactate solution is a well-known physiological solution that is made of a mixture of sodium chloride, sodium lactate, potassium chloride, and calcium chloride in water. It is used for replacing fluids in electrolytes who have low blood pressure or low blood volume.

Buffers and other solutions that contained buffered species are often needed in large volumes. For example, biopharmaceutical applications often require large volumes of different buffers during the various processing operations that take place. Traditionally, buffers are prepared manually as concentrates that are then diluted as needed. First, concentrated buffers need to be manually made and this requires specialized equipment and personal with knowledge (e.g., use of balances and labware needed to form concentrated buffers) which is not always available. For example, resource limited settings often do not have the laboratory equipment and trained workers that can be used to create such stock solutions. In addition, because concentrated buffer solutions are manually made, this introduces the possibility of human error into the process. Finally, the preparation of buffers and other physiological solutions requires the storage of large amounts of buffers and raw materials. Furthermore, in some instances, the final buffers or other physiological solution are needed in remote locations (e.g., physiological solutions needed in resource limited area) that do not have adequate local resources to reliably generate their own concentrated solutions that can then be diluted down to the desired concentration.

Some attempts have been made to automated the generation of various buffer solutions. For example, buffers have been prepared using in-line conditioning in which buffers are prepared from concentrated, low-volume, single-component stock solutions to prepare a variety of different buffer solutions. An example of this is GE Healthcare's in-line buffer conditioning system. This system operates by diluting stock solutions of acids, bases, and salts with water for injection. An automated control system uses various feedback sensors to adjust the flow rates of the stock solutions to achieve the desired final buffer concentration. The automated control system used in the GE in-line buffer condition system requires a large number of sensors (e.g., pH, conductivity, flow sensors) that are used in feedback monitoring to ensure that the final desired buffer has the correct composition. Unfortunately, these sensors can malfunction or give bad readings which may mean that the buffer solution is not at the composition that was intended. In addition, in-line buffer control may suffer from mixing problems which can result in out-of-specification products. Moreover, the control system is expensive requiring complicated and expensive hardware and specialized control software to control the entire system. Alternative, systems and method for preparing fluids for bioprocess and pharmaceutical applications are needed.

SUMMARY

In one embodiment, a system for the preparation of fluids for bioprocess and pharmaceutical applications uses one or more flexible containers (e.g., bags) that are pre-loaded with solid tablets contained therein of various buffer/media/physiological fluid constituents. These may include salts, acids, and bases, preservatives, proteins, amino acids, growth factors, small molecules, drugs, or other components that are capable of being stored in solid form. The flexible container is sterilized by, for example, gamma radiation. The flexible container contains one or more sealed or sealable openings that are used to add water to the interior of the flexible container as well as remove fluid from the flexible container. The one or more sealed or sealable openings may also be used as an outlet to remove fluid from the flexible container. The flexible container may be stored in a deflated state aiding in the storage and/or transport of the flexible containers.

The flexible container may have a fill mark, mark, or other indicia indicating the level or water to be added to the flexible container (or multiple of such lines, marks, or indicia). The fill mark, mark, or other indicia makes it easy to use as one only needs to fill the flexible container with water until the fill mark is reached. In other embodiments, the fill mark may be omitted and substantially the entire volume of the flexible container may be filled with fluid. In either embodiment, the flexible container has a defined fill volume that is used to fill the flexible container with water. Because each flexible container contains a known amount of solid buffer constituents (or constituents for other fluids, e.g., growth media, physiological fluids, or the like), the concentration of the resulting solution is easily determined. There is no need to weigh or measure powders or other additives as these are already present in the flexible container. Of course, the tablets that are contained in the flexible container need to dissolve. The tablets may dissolve over time into solution. Agitation or other mixing means may also be used to aid in dissolving the tablets. For example, the flexible container may also contain a magnetic stirrer (e.g., magnetic stir bar) or the like inside which can be used to further aid dissolving the tablets.

The flexible containers are pre-loaded with one or more tablets. The tablets are preferably loaded into the interior of the flexible container during or just after forming the flexible containers. In one embodiment all of the tablets are of the same type. In another embodiment, the tablet includes a plurality of different types. In one preferred embodiment, the particular recipe or ingredients that are needed to form the final buffer or other solution merely requires knowing the numbers and/or types of tablets to be placed inside the flexible container. For example, one buffer solution may have a recipe that requires four tablets of type A, two tablets of type B, and five tables of type C. This allows one to easily pre-load the flexible container with the required tablets that, once dissolved, yield the final buffer or other solution. In this case, one merely adds the different types of tablets in the specific numbers. This process may take place manually or it may be automated. Pill counting machines are well-known and can be used to automatically dispense tablets inside the flexible container during or after the manufacturing process.

After the flexible containers have been loaded with the requisite tablets, the flexible container and contents may be sealed (if not already sealed). The flexible container and contents are then subject to gamma irradiation (or another irradiation process to sterilize the flexible container). The flexible container may then be shipped or transported to the desired location for use. A user then can fill the flexible container with the required volume of water. The tablets dissolve to create the final buffer or other solution. The flexible containers, in some embodiments, may be held using a hook or the like that pass through corresponding apertures formed into the flexible containers. The flexible containers may also be contained in or hung from a trolley, cart, or the like or they be free-standing. The volume of the flexible containers may vary but is typically larger than 100 mL and up to about 2,000 L although size ranges between about 2 L and 500 L are more typical.

In one embodiment, a plurality of the flexible containers described above are used in connection with a manifold that allows the selective flow of water into the flexible containers. Flow of fluid containing dissolved species from the tablets may also flow out of the flexible containers. For example, in one embodiment, a plurality of flexible containers are fluidically connected via conduit or tubing to the manifold with each branch of the manifold having a valve (e.g., pinch valve) that can control whether water flows into the flexible containers and whether the buffer containing the contents of the dissolved tablets are removed from the flexible bag (i.e., two pinch valves per flexible bag; one for fluid going into the flexible container and one for fluid that is removed from the flexible container). In other embodiments, the manifold is only used to provide water into the various flexible containers while a separate outlet in the flexible bag is used to withdraw the buffer solution (e.g., using gravity feed or a pump connected thereto). The plurality of flexible containers that are connected to the manifold may have different tablet compositions tailored to the specific desired buffer. In this regard, a single manifold coupled to a common water source may be used to produce a plurality of different buffer types by selectively filling the appropriate flexible containers. Of course, multiple of the flexible containers may the same tablet recipe so that larger volumes of buffer solution may be prepared.

Typically, the final buffer solution that will be formed in the flexible containers will be further diluted with water prior to use. For example, the buffer solution that is created in the flexible container may concentrated between about a 5-10× dilution. This buffer solution may then be diluted further (e.g., a 5× dilution) to generate to final buffer dilution in the range of 1×-2×. In one embodiment, this further dilution will take place in another vessel or container. However, it is possible that this further dilution may be accomplished while the flexible container is coupled to the manifold. For example, additional water may be added to the flexible container containing the buffer at the 5-10× to generate a final buffer solution that exits the manifold at or near the desired ~1-2× dilution.

A significant advantage of the current system is that the chance for human error in making concentration buffer solutions is avoided. Local personnel do not need to weigh reagents which are then later dissolved as this process has already taken place at the manufacturing site. This is particularly advantageous for resource-limited locations where laboratory equipment and/or trained personnel may not be available. Furthermore, there is no need to store large volumes of pre-concentrated buffer solutions as these may be made as needed or on demand. This reduces storage and transportation costs. Nor is there a need for complicated and expensive equipment that is used to make in-line adjustments that rely on a variety of feedback sensors which may fail or provide erroneous results which result in buffer solutions not having the desired concentration or profile.

In one embodiment, a device for producing fluids for bioprocess and pharmaceutical applications includes a flexible bag defining an interior volume and having at least one inlet and outlet, the flexible bag containing in the interior volume a plurality of tablets. To use the flexible bag, the flexible bag is filled with a pre-determined volume of water. The pre-determined volume of water may be determined by a fill mark located on the flexible bag.

In another embodiment, a system for producing fluids for bioprocess and pharmaceutical applications includes a manifold having first and second halves surrounding a segment of flexible tubing having a main line extending therethrough and a plurality of branch lines coupled to the main line. A plurality of flexible bags are secured to the plurality of branch lines, each flexible bag comprising an interior volume and having at least one inlet and outlet and further containing in the interior volume of each plurality of flexible bags a plurality of tablets. A plurality of pinch valves are disposed on the manifold and configured to pinch the main line along one or more locations and the plurality of branch lines secured to the plurality of flexible bags. To use the system, one or more of the plurality of valves are actuated to create an inlet flow path from the main line through at least one branch line and into one or more flexible bags. A pre-determined volume of water is then flowed into the one or more flexible bags via the main line (e.g., until the water level reaches the fill mark).

In another embodiment, a method of producing a fluid for bioprocess and pharmaceutical applications includes the operations of selecting a flexible bag defining an interior volume and having at least one inlet and outlet, the flexible bag containing in the interior volume a plurality of tablets, wherein the selected flexible bag corresponds to a particular concentration of solutes contained within the fluid. The flexible bag is filled with a known volume of water.

1, four tablets of type #2, and one tablet of type #3. The tablets are shown inside the flexible bag. The flexible bag includes a fill mark.

Figures 1, 2:
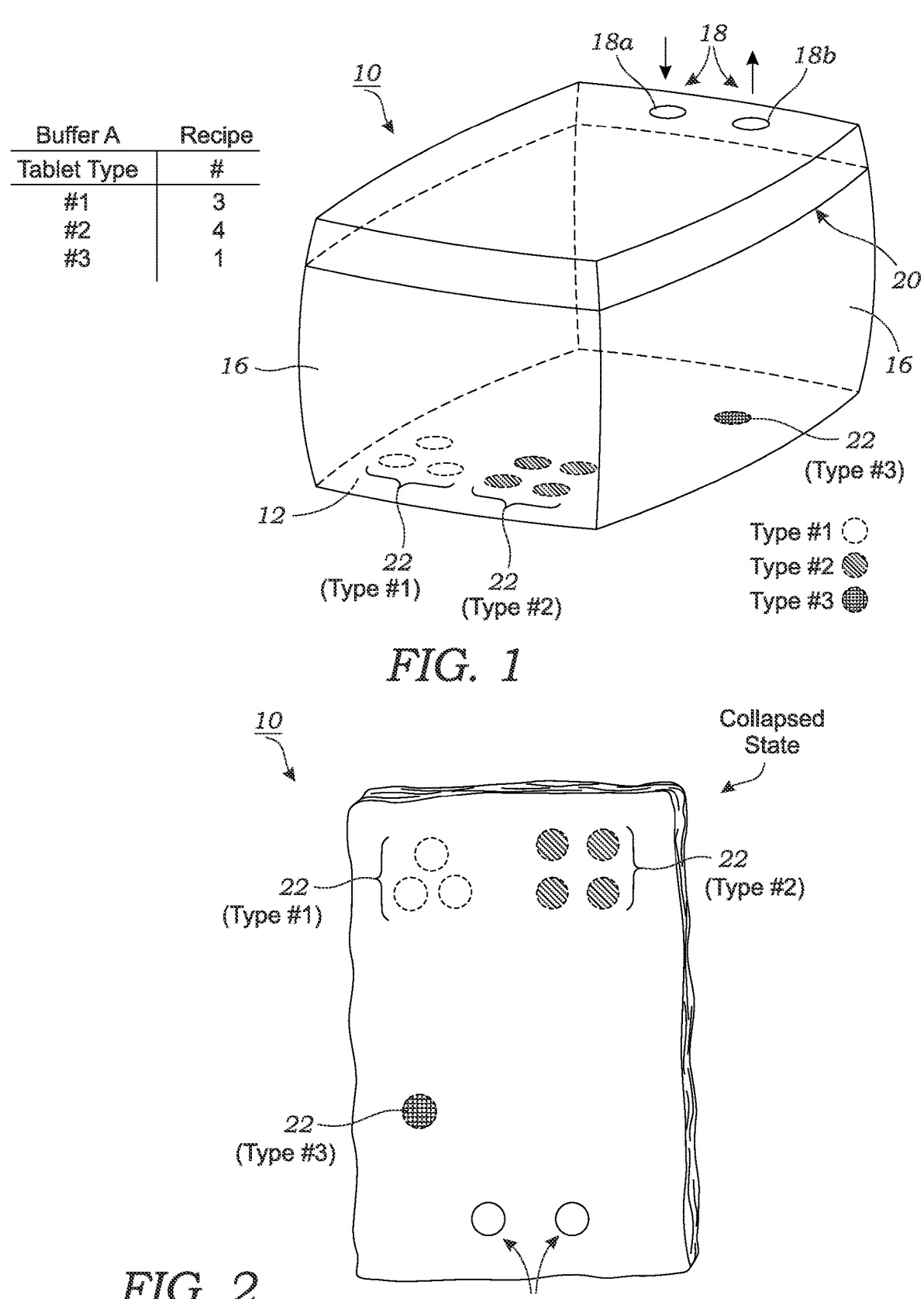
FIG. 1 illustrates a flexible container in the form of a flexible bag according to one embodiment. Also illustrated is a recipe for Buffer A which includes three tablets of type

FIG. 2 illustrates the flexible bag of FIG. 1 in a collapsed state. The collapsed bag takes up minimal space and is useful for storage and transportation.

Figure 3:
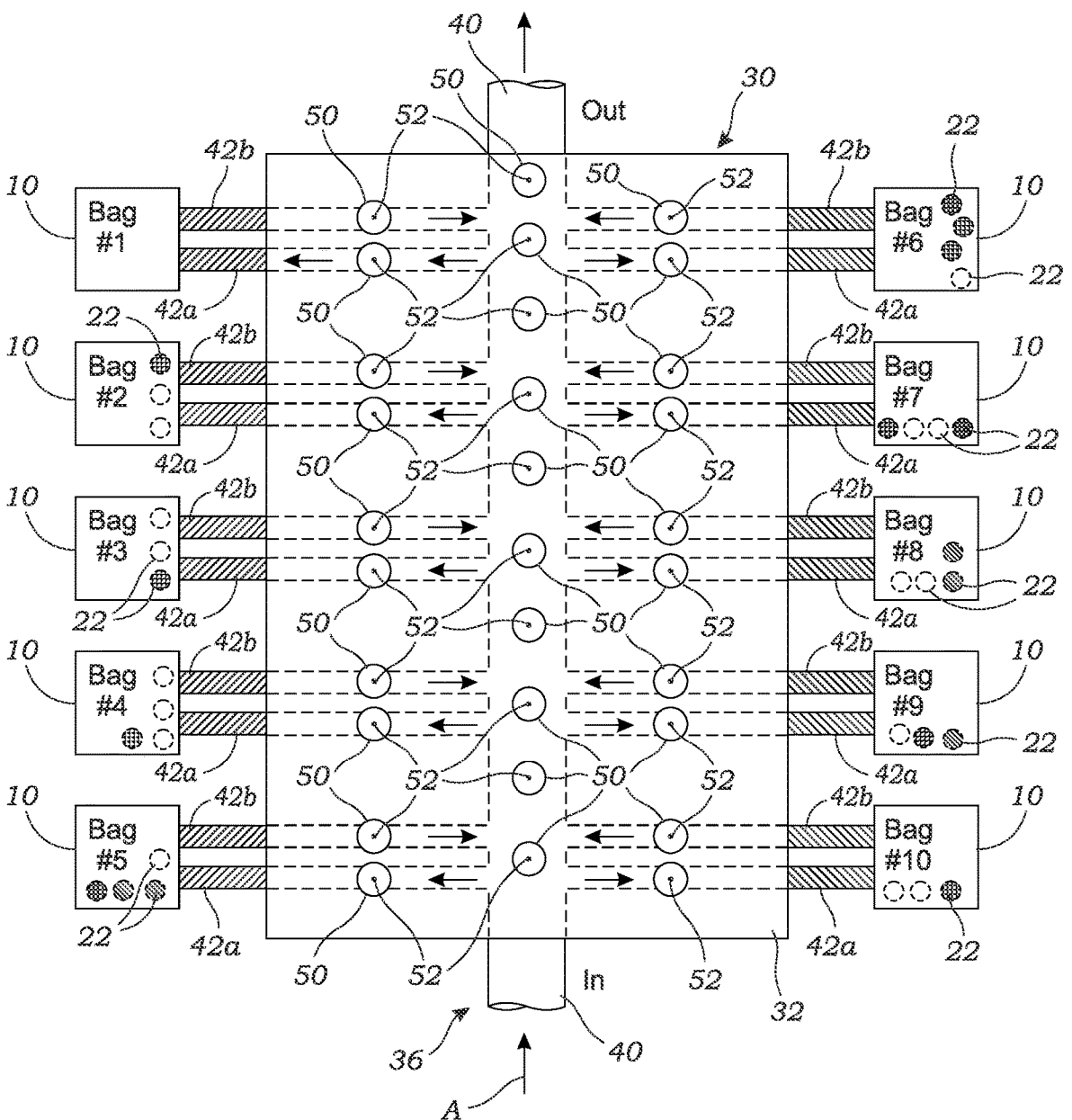

FIG. 3 illustrates a manifold according to one embodiment that is used to control the flow into and out of a plurality of flexible bags. Valve closure points are indicated so that that the individual flexible bags may be loaded with fluid and/or remove fluid containing dissolved species from the tablets that is present in the flexible bags. A main or central segment of tubing or conduit extends through the manifold and is used to transfer fluid to or from the flexible bag.

Figure 4:
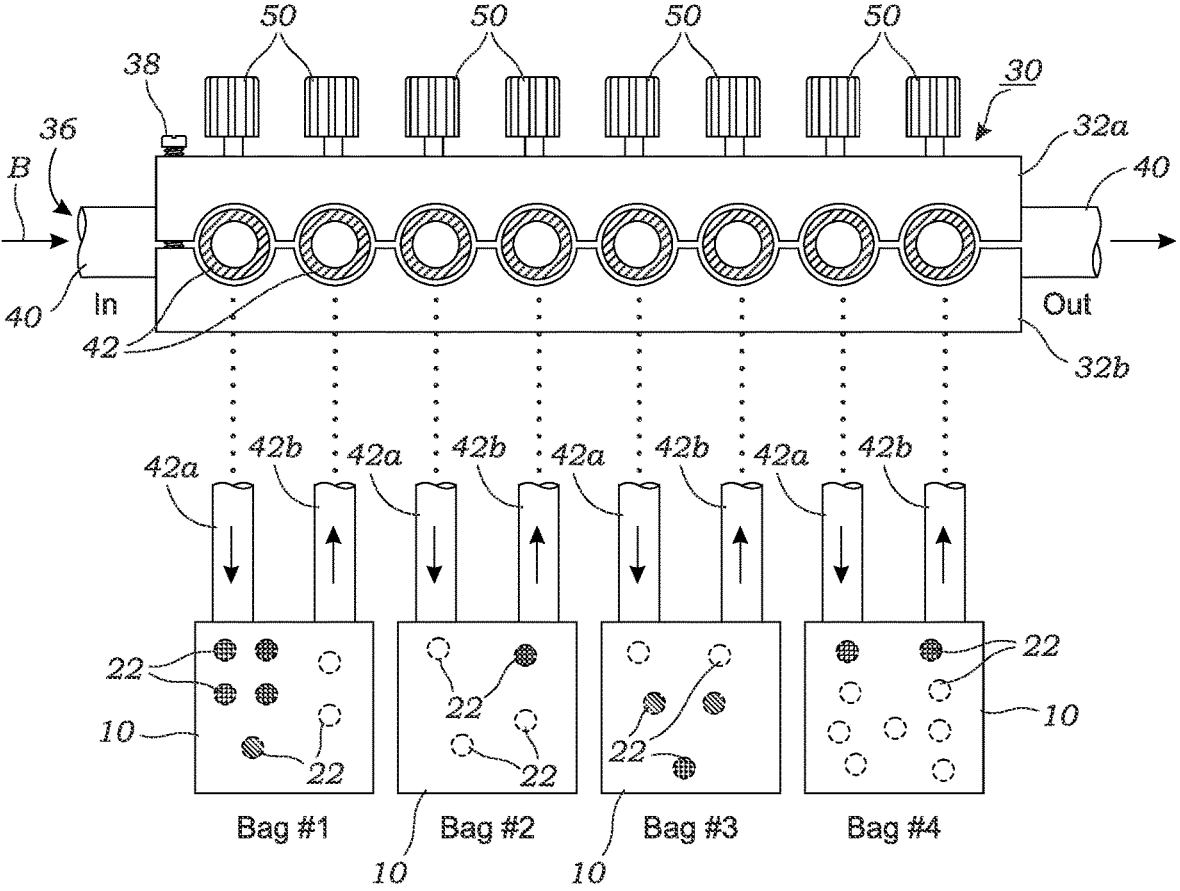

FIG. 4 illustrates a side view of a manifold of the type illustrated in FIG. 3. However, in this embodiment, the manifold has four (4) flexible bags coupled to one side of the branch lines.

Figures 5A, 5B:
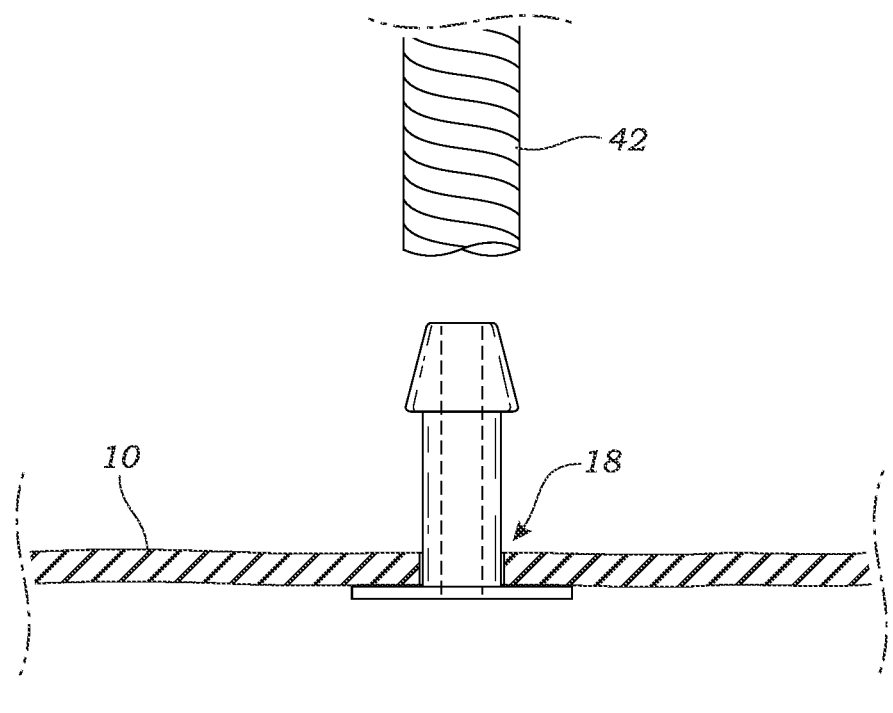

FIG. 5A illustrates one example of a port that can be formed in the flexible bag.

FIG. 5B illustrates another example of a port that can be formed in the flexible bag.

Figure 6:
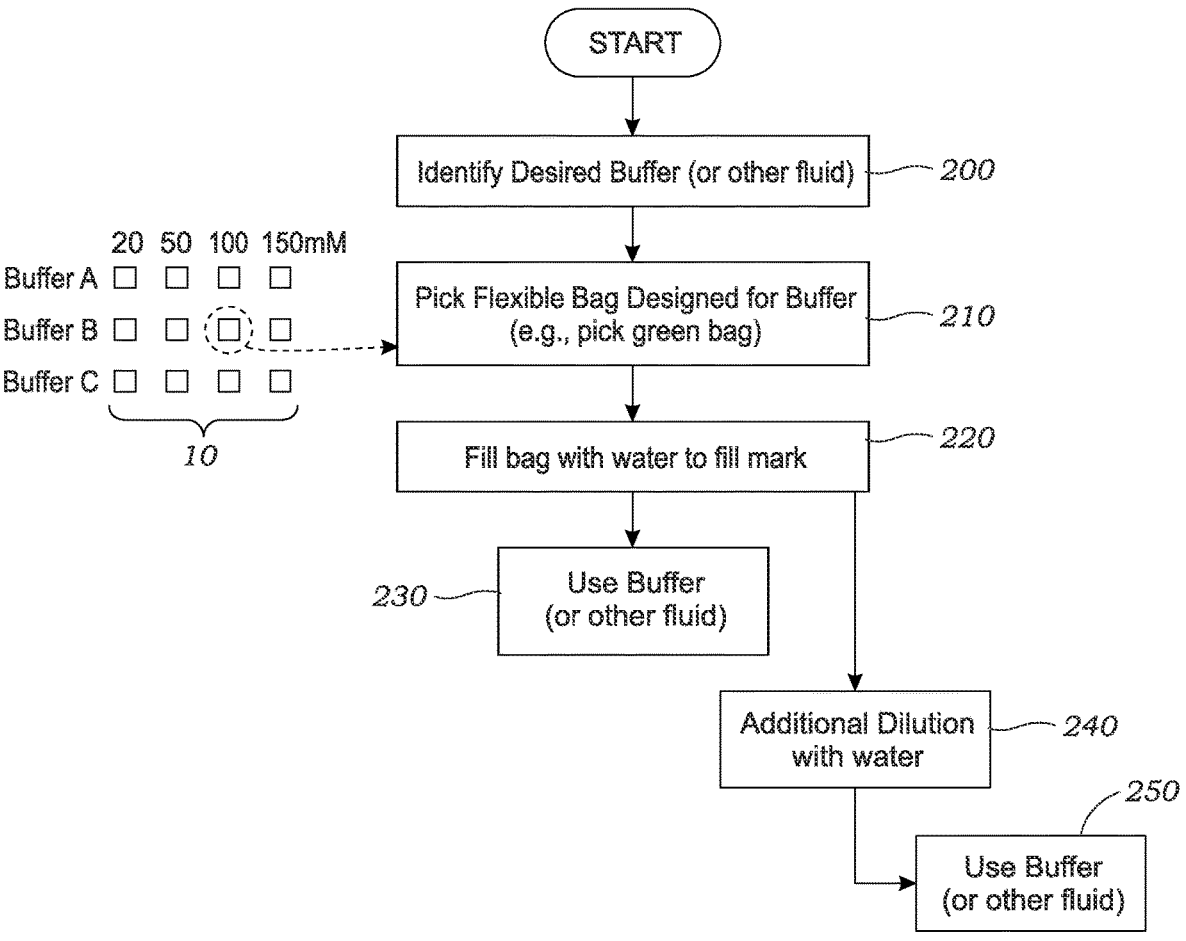

FIG. 6 illustrates a sequence of operations used to select a flexible bag of the type disclosed herein for use in creating a desired buffer solution concentration.

Figure 7:
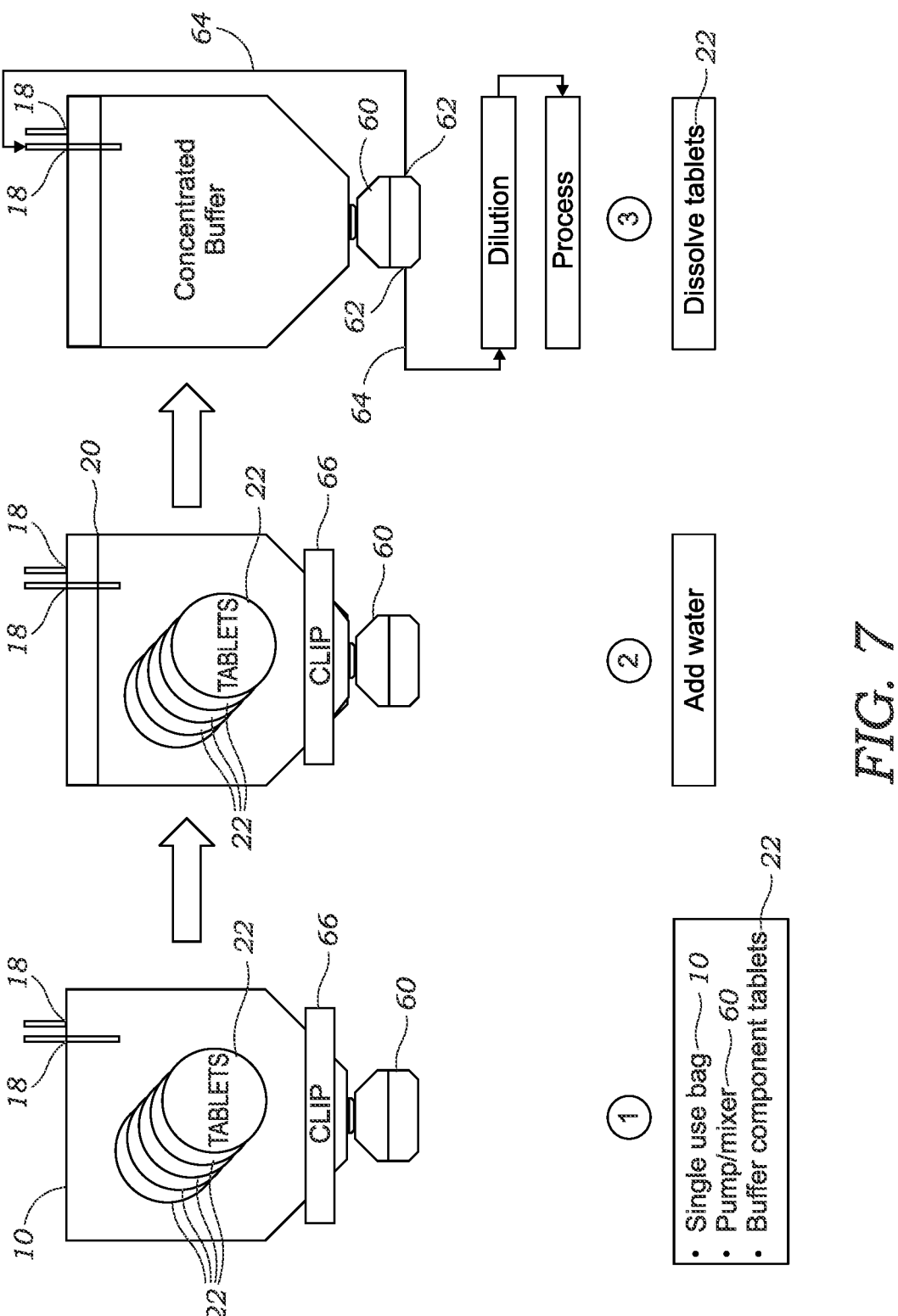

FIG. 7 illustrates a flexible bag secured to a pump and/or mixing device which can be used to evacuate and/or recirculate fluid in the flexible bag. A single use flexible bag having tablets contained therein (e.g., buffer tablets). Water is then added to the flexible bag where upon they dissolve to form a concentrated buffer solution. Fluid may be recirculated back into the flexible bag to aid in mixing or pumped out for further dilution or processes.

DETAILED DESCRIPTION OF ILLUSTRATED EMBODIMENTS

FIG. 1 illustrates a flexible container in the form of a flexible bag 10 according to one embodiment of the invention. The flexible bag 10 is typically made from polymer or resin material(s) and may have any number of shapes and sizes. The flexible bag 10 may be formed from multiple layers or a single layer. The flexible bag 10, depending on the size, may be carried in a trolley, dolly, cradle, cart, holder, or other support container to hold the flexible bag 10 when filled with fluid. The flexible bag 10 defines an interior volume and typically has one or more discrete surfaces. For example, the flexible bag 10 typically has a bottom surface 12, an upper surface 14, and one or more side surfaces 16 (e.g., four sides are illustrated in FIG. 1 although different shapes are contemplated).

The flexible bag 10, in one embodiment, is made from one or more polymers or resin materials. For example, medical-grade resins compliant with class VI standards may be used. Additional examples include polyethylene (e.g., low density polyethylene (LDPE)) or ultra-low density polyethylene (ULDPE) or polypropylene (PP), ethylene vinyl acetate (EFA), polyethylene terephthalate (PET), polyvinyl acetate (PVA), polyvinyl chloride (PVC), and the like are also contemplated. In some embodiments, the flexible bag 10 may be formed from multiple layers. For example, the inner layer that contacts the fluid may be made from LDPE. A second layer of polyvinyl acetate (PVA) or flexible polyvinyl chloride (PVC) may be used as an intermediate layer. An outer layer of LDPE or PET may provide mechanical strength. It should be appreciated that the embodiments described herein may be used with any number of different construction types, materials, and layers used for the flexible bag 10.

The flexible bag 10 has an interior volume that is typically larger than 100 mL and up to about 2,000 L in size. More typically, however, the volume size of the flexible bag 10 ranges between about 2 L and 500 L. The flexible bag 10 includes one or more ports 18 or openings that provide access for fluid to inter/exit the flexible bag 10. FIG. 1, for example, illustrates two such ports 18a, 18b with one port 18a being used for water to be supplied to the interior of the flexible bag 10 (i.e., inlet) while a second port 18b being used to remove (i.e., outlet) the fluid solution from the flexible bag 10 (a single port 18 may be used as an inlet and outlet in another embodiment). The water that may be used typically includes water-for-injection (WFI), highly purified water (HPW), or purified water (PW). These water types are typically used in pharmaceutical and bioprocess applications. The water may be pumped into the flexible bags 10 using a pump or the like or it may be gravity fed. The ports 18 may be coupled to conduits or tubing that are used to transfer fluid to and from the flexible bag 10. The ports 18 may include connectors, flanges, or ends that are integrated into the flexible bag 10 and enable tubing or conduits (e.g., branch line 42) to be easily connected to the flexible bag 10 such as the ports illustrate in FIGS. 5A and 5B. For example, a port 18 with a nipple, barb (FIG. 5A), or aseptic connector known to those skilled in the art may be used (e.g., tri-clamp (TC) as illustrated in FIG. 5B).

As seen in FIG. 1, the interior of the flexible bag 10 contains one or more tablets 22. The term tablet 22 is meant to encompass discrete solid or semi-solid (e.g., gel) materials that include constituents such as, but not limited to, salts, acids, and bases, preservatives, proteins, amino acids, growth factors, small molecules, drugs, or other molecules and compounds that are capable of being stored in solid or semi-solid form. The tablets 22 may or may not resemble traditional pills. The solid constituents may be combined with an excipient such as a binder (e.g., natural polymers like starches or gums, synthetic polymers, or sugars) and/or preservatives to form the tablet 22. Such excipients are well known in the formation of pharmaceutical tablets. The tablet 22 contains one or more solutes that dissolve in a solvent which is typically water. The tablets 22 each have a known quantity of material contained therein (e.g., mass or volume). Different "types" of tablets 22 may have different sizes to achieve the correct final concentration desired. The tablets 22 are pre-loaded into the flexible bag 10 prior to use. That is to say, the tablets 22 are placed inside the flexible bag 10 during the manufacturing process or after the flexible bag 10 has been formed. The number and nature of the tablets 22 that are contained in the flexible bag 10 varies depending on the composition of the final solution that is desired to be formed in the flexible bag 10. For example, the tablets 22 may include buffer constituents, namely, a weak conjugate acid-base pair. The choice of buffer that is desired is associated with a recipe for the types and numbers of tablets 22 that are located inside the flexible bag 10. Different tablets 22 made from different constituents may have different shapes and/or colors. This may be advantageous, for example, if the tablets 22 are manually added into the flexible bag 10.

In the example of FIG. 1, the end user would like to make buffer "A." Buffer A is associated with a recipe (seen in the table of FIG. 1) that includes three tablets 22 of tablet type #1, four tablets 22 of tablet type #2, and one tablet 22 of tablet type #3. Each tablet 22 may contain different components. For example, tablet type #1 may contain chemical compounds associated with a salt while tablet type #2 is associated with chemical compounds used to form acids or bases. Importantly, the end user does not have to know or even care about the particular recipe used to make the flexible bag 10 because all of the necessary tablets 22 have already been pre-loaded into the interior of the flexible bag 10 as part of the manufacturing process. The end user only needs to select the flexible bag 10 that is associated with buffer type "A." This may be marked on the flexible bag 10 itself using labeling, marking, color coding, bar codes, QR code, or the like so that the user can easily identify the required flexible bag 10 that is needed to make buffer A.

The flexible bag 10 may be used to create any number of different types of solutions used in biopharmaceutical processes as well as physiological solutions. Examples include phosphates, acetates, citrates, tris(hydroxymethyl)-aminomethane HEPES (4-(2-hydroxyethyl)-1-piperazineethanesulfonic acid), pH adjusters (e.g., HCl and NaOH). Exemplary phosphate buffers include potassium dihydrogen phosphate ($KH_2PO_4$), di-potassium hydrogen phosphate ($K_2HPO_4$), di-sodium hydrogen phosphate ($Na_2HPO_4$), sodium dihydrogen phosphate ($NaH_2PO_4$). Acetates include by way of example, ethanoic acid, acetic acid, sodium acetate. An example of a citrate includes citric acid. The tablets 22 may also be used for growth or maintenance media used to support living cells (e.g., eukaryotic cells, bacteria, or yeast).

Still referring to FIG. 1, the flexible bag 10 may have a fill mark 20 which may include a marking, line, or other indicia indicating the level or water to be added to the flexible bag 10. The fill mark 20 may be located on one or all the sides 16 of the flexible bag 10. The fill mark 20 makes it easy to use as one only needs to fill the flexible bag 10 with water until the fill mark 20 is reached. In other embodiments, the fill mark 20 may be omitted and substantially the entire volume of the flexible bag 10 may be filled with fluid. In either embodiment, the flexible bag 10 has a pre-determined fill volume that is used to fill the flexible bag 10 with water. In some embodiments, the flexible bag 10 may include a sealable port 18 such that once water is added the flexible bag 10 may be stored for later use. The sealable port 18 may include a cap, pinched line, self-sealing valve, manual valve, membrane, plug or the like. The one or more sealed ports 18 that are located in the flexible bag 10 may also be used as an outlet to remove fluid from the flexible bag 10. The ports 18 may be located on different surfaces of the flexible bag 10. FIG. 1 illustrates the openings or ports 18*a*, 18*b* located on the upper surface 14 but it should be appreciated that these ports 18 may be provided on other surfaces. For example, for gravity evacuation the outlet port 18 may be located on a bottom surface 12 of the flexible bag 10.

FIG. 2 illustrates a flexible bag 10 in a collapsed state. The collapsed state helps for storage and transportation of the flexible bag 10 given the small volume occupied by the flexible bag 10 in the collapsed state. In some embodiments, a vacuum may be applied to the interior of the flexible bag 10 to remove substantially any air or other gases contained inside the interior volume or space of the flexible bag 10. The tablets 22 are pre-loaded into the interior of the flexible bag 10 as illustrated in FIGS. 1 and 2. This process may take place manually or it may be automated. Pill counting machines are well-known and can be used to automatically dispense tablets 22 inside the flexible bag 10 during or after the manufacturing process. The pill counting machines may be computer-controlled and contain the recipes for the particular fluid type (e.g., buffer) that is associated with the manufactured flexible bag 10.

For example, in the example of FIGS. 1 and 2, a flexible bag 10 would automatically be fed with three tablets 22 of tablet type #1, four tablets 22 of tablet type #2, and one tablet 22 of tablet type #3. Optionally, a magnetic stirrer (e.g., magnetic stir bar or the like) may be added to the interior of the flexible bag 10 during the manufacturing process. For example, the flexible bag 10 may be disposed atop a magnetic stirrer that can rotate the stir bar located inside the flexible bag 10 and aid in dissolving the tablets 22.

After the flexible bags 10 have been loaded with the requisite tablets 22, the flexible bag 10 and contents may be sealed (if not already sealed). The flexible bag 10 and the contents are then subject, in one embodiment, to gamma irradiation (or another irradiation process to sterilize the flexible bag 10). The flexible bag 10 may then be shipped or transported to the desired location for use. A user then can fill the flexible bag 10 with the required volume of water (e.g., to the fill mark 20). The tablets 22 dissolve to create the final desired solution (e.g., buffer, physiological solution, media solution for cells, etc.). The flexible bags 10, in some embodiments, may be held using a hook or the like that pass through corresponding apertures formed into the flexible bag 10. The flexible bags 10 may also be contained or hung in a trolley, cart, or the like or they may be free-standing. The volume of the flexible bags 10 may vary but is typically larger than 100 mL and up to about 2,000 L although size ranges between about 2 L and 500 L are more typical.

FIGS. 3 and 4 illustrates a manifold 30 that is used to modulate flow into and out of a plurality of flexible bags 10. The manifold 30 includes a rigid two-part housing 32 (best seen in FIG. 4) that surrounds flexible tubing or conduit 36 that is interposed between the two halves 32*a*, 32*b* of the housing 32. The housing 32 may be made out of metal or a rigid polymer. The flexible tubing or conduit 36 may include unreinforced silicone or other polymer materials such as thermoplastic elastomers (TPE), thermoplastic rubber (TPR), or the like. The manifold halves 32*a*, 32*b* include facing surfaces that have respective semi-annular recesses formed therein that accommodate the flexible tubing or conduit 36 and surround the same in a circular fashion when the manifold halves 32*a*, 32*b* are secured to one another via one or more fasteners 38. The fasteners 38 may include latches, clips, bolts, screws, or the like. In this regard, the two-part manifold 30 fits snugly around flexible tubing or conduit 36. The tubing or conduit 36 includes a main line 40 or segment that passes through the manifold 30 at one end and exits at an opposing end and includes a number of branch lines 42 that extend from the main line 40 (e.g., branch lines 42*a*, 42*b* as described herein). Water is run through the main line 40 in the direction of arrow A in FIG. 3 (and arrow B for FIG. 4).

As best seen in FIG. 3, two branch lines 42*a*, 42*b* are fluidically coupled to each separate flexible bag 10. A first branch line 42*a* is used to fill the flexible bag 10 with water from the main line 40. A second branch line 42*b* is used to withdraw fluid (e.g., buffer solution) from the flexible bag 10 where, in this embodiment, the withdrawn fluid enters the main line 40. In this embodiment, the second branch line 42*b* is used to remove fluid from the flexible bag 10. In other embodiments, the second branch 42*b* may be omitted entirely. For example, fluid may be removed from the flexible bag 10 using another port 18 connected to the flexible bag 10. For example, an opening in the bottom surface 12 of the flexible bag 10 may be used to withdraw fluid from the flexible bag 10 (via gravity feed or even using an attached pump). In the embodiment of FIGS. 3 and 4, valves 50 are used to selectively control the flow of fluid into and out of the flexible bags 10. The valves 50 are positioned in the branch lines 42*a*, 42*b* and along the main line 40. The valves 50 along the main line 40 are located between branch lines 42*a*, 42*b* for different flexible bags 10 so that flow can be isolated to/from a particular flexible bag 10. FIG. 3 illustrates the various valve closure points 52 for the valves 50 that may be used to isolate flow each individual flexible bag 10 (or flow to/from multiple flexible bags 10). Thus, the valves 50 are actuated to create different flow paths to and from the various flexible bags 10 that are coupled to the tubing or conduit 36 of the manifold 30.

In one preferred embodiment, pinch valves 50 located on the manifold 30 are used to selectively pinch the flexible tubing or conduit 36 at the valve closure points 52. The pinch valves 50 may include automatically controlled valves 50 (e.g., pneumatic valves) or they may include manual operated pinch valves 50 are that are controlled by rotation of a bonnet or the like. The pinch valves 50 include a stem that extends axially to pinch the flexible tubing or conduit 36 when actuated and stop the flow of fluid at the valve closure point(s) 52. Movement of the stem of the pinch valve 50 in the opposite direction allows the flexible tubing or conduit 36 to open and fluid to flow. The pinch valves 50 may be located in the main line 40 or branch lines 42.

In the embodiment of FIG. 3, there are ten (10) flexible bags 10 are fluidically coupled to branch lines 42 of the manifold 30 although it should be understood that there could be fewer or more flexible bags 10. In one embodiment, the flexible bags 10 that are connected to the manifold 30 may be designed for different buffer solutions. For example, in this particular embodiment, ten (10) different buffer solutions may be generated using the single manifold 30 (each flexible bag 10 having a different tablet 22 combination therein). Alternatively, some or all of the flexible bags 10 may be used to make the same buffer. For example, the manifold 30 may be used to make a plurality of flexible bags 10 that contain the same buffer. Of course, it should be understood that various combinations are possible depending on the type of flexible bag 10 that is coupled to the manifold 30. The various flexible bags 10 that are fluidically coupled to the manifold 30 may, in some embodiments, be connected via an aseptic connector so that the flexible bags 10, once filled, may be removed from the manifold 30. These may include tri-clamp (TC) connectors but it should be appreciated that other hygienic connectors such as male/female connectors, flange connectors, and the like (including proprietary connectors) may be used. FIG. 4 illustrates a side view of a manifold 30 showing the two-part housing 32*a*, 32*b* of the manifold housing 32 and the branch lines contained therein that lead to the different flexible bags 10. Pinch valves are illustrated on the manifold that are used to control flow in the various branch lines.

With reference to FIG. 3, the manifold 30 may be used to selectively fill (and remove fluid from) the various flexible bags 10 attached thereto. For example, flexible bag 10 designated Bag #1 in FIG. 3 may be filled with water by opening up the valve 50 that is located in the incoming branch line 42*a*. Water fills the flexible bag 10 until the fill mark 20 is reached (or the flexible bag 10 is filled entirely). In this example, the tablets 22 are buffer tablets. The buffer tablets 22 contained in the flexible bag 10 dissolve after the passage of time or through mixing or agitation assistance (e.g., magnetic stir bar). Once the tablets 22 have been dissolved, the buffer solution that is created can then be removed from the flexible bag 10. This may occur in several different ways. In one embodiment, the flexible bag 10 may be removed from the manifold 30 and then the fluid contained therein is subject to further dilution. In another embodiment, the flexible bag 10 may contain an outlet port 18 (e.g., in the bottom surface 12) and the buffer fluid is evacuated from the flexible bag 10 using gravity flow or assisted with a pump. In another embodiment, water is input to the flexible bag 10 using flow from the main line 40 that is then passed into the open branch line 42*a* coupled to the flexible bag 10. The outlet branch line 42*b* is open and allows the buffer solution to be removed from the flexible bag 10 and passing into the main line 40 and out the manifold 30 in the direction of arrow B (or downstream to another coupled process or operation). Note that because water is being added to the flexible bag 10, the buffer contained therein is diluted at the same time as being removed.

Typically, the final buffer solution that will be formed in the flexible bags 10 will be further diluted with water prior to use. For example, the buffer solution that is created in the flexible bag 10 may concentrated between about a 5-10× dilution. This buffer solution may then be diluted further (e.g., a 5× dilution) to generate to final buffer dilution in the range of 1×-2×. In one embodiment, this further dilution will take place in another vessel or container. However, it is possible that this further dilution may be accomplished while the flexible bag 10 is coupled to the manifold 30 as explained above when water is added to the flexible bag 10. For example, additional water may be added to the flexible bag 10 containing the buffer at the 5-10× to generate a final buffer solution that exits the manifold 30 at or near the desired ~1-2× dilution.

FIG. 6 illustrates an exemplary flow chart or sequence of operations that are performed by an end user using the flexible bag 10 described herein. In this example, the end user identifies the type of solution (e.g., buffer type B) that is desired to be made as seen in operation 200. For example, the end user may want to make 100 mM phosphate buffer. In this example, the user picks a flexible bag 10 that is specially designed with the tablet recipe to produce 100 mM phosphate buffer. This is seen in operation 210 of FIG. 6. The user may identify the flexible bag 10 to be used based on the labeling, marking, color coding, bar codes, QR code, or the like found on the flexible bag 10 (e.g., the user picks the green colored flexible bag 10). The user then fills the flexible bag 10 with water until the fill mark 20 is reached as seen in operation 220 (or until the flexible bag 10 is filled entirely). The tablets 22 contained the flexible bag 10 then dissolve to produce the 100 mM phosphate buffer. This flexible bag 10 containing buffer type B at 100 mM concentration may then be used directly (operation 230) or, alternatively, the buffer solution contained therein may be further diluted for example by transferring the solution to another vessel or container and adding further water. This further dilution may also be performed using the manifold 30 as described previously where water is used to simultaneously evacuate and dilute the contents of a flexible bag 10. This further dilution operation is illustrated in operation 240 of FIG. 6. For example, a 5× dilution may be performed to create 20 mM phosphate buffer. This further diluted buffer can then be used as seen in operation 250.

As described above, note that the end user did not have to weigh any buffer materials to make the initial concentrated buffer solution. Nor did the end user even have to add any tablets 22 to the flexible bag 10 as these were already pre-loaded in the flexible bag 10. The end user merely had to find the right flexible bag 10 to use to achieve the desired 100 mM phosphate buffer concentration. This step only required the user to identify the flexible bag 10 that was associated with the 100 mM phosphate buffer concentration, an operation that can be done by someone with minimal or no training. Further dilutions can be performed easily as well as described above. As can be seen above, there is no need for any expensive laboratory equipment and there is no chance of error in weighing the solid materials as the tablets 22 have already been pre-loaded into the flexible bags 10.

FIG. 7 illustrates a single use flexible bag 10 secured to a pump and/or mixing device 60 which can be used to evacuate and/or recirculate fluid in the flexible bag 10. The pump and/or mixing device 60 may be secured to the bottom surface 12 of the flexible bag 10. The pump and/or mixing device 60 can be secured to the flexible bag 10 using a port 18 or the like that disclosed in FIG. 5B. An example of the pump and/or mixing device 60 may be found in International Patent Application Publication No. WO 2021/158448 A1 (PCT/US2021/015917), which is incorporated by reference. The pump and/or mixing device 60 may have a mating flange that can be secured to the port 18 via a clamp or the like. The port 18 in this embodiment acts an outlet for the fluid contained in the flexible bag 10 which then enters the inlet of the pump and/or mixing device 60. The pump and/or mixing device 60 has one or more outlets 62 through which the fluid exits. The outlets 62 may be coupled to fluid lines or conduits 64. As seen in FIG. 7, one such outlet 62 is used to recirculate fluid back into the flexible bag 10 via a port 18. Another such outlet 62 is used to send fluid to further processes (e.g., further dilution). FIG. 7 illustrates a removable clip 66 that is secured around the flexible bag 10. The removable clip 66 is secured around the flexible bag 10 while water is added to dissolve the tablets 22. After the tablets 22 have sufficiently dissolved, the removable clip 66 can be removed, thereby allowing the fluid to gain access to the pump and/or mixing device 60. In this example, water is then added to the flexible bag 10 to dissolve buffer tablets 22 to create a concentrated buffer solution, whereby they dissolve to form a concentrated buffer solution. Fluid may be recirculated back into the flexible bag 10 or pumped out for further dilution or processes.

While embodiments of the present invention have been shown and described, various modifications may be made without departing from the scope of the present invention. For example, while buffer solutions have been a focus of the application it should be appreciated that any number of types of fluids may be created within the flexible bags 10. This includes growth or maintenance fluids for supporting cells. It may also include physiological solutions such as IV solutions (e.g., Ringer's solution) and the like which are administered to subjects. The invention, therefore, should not be limited, except to the following claims, and their equivalents.

What is claimed is:

1. A system for producing fluids for bioprocess and pharmaceutical applications comprising:

a manifold having first and second halves surrounding a segment of flexible tubing having a main line extending therethrough and a plurality of branch lines coupled to the main line;

a plurality of flexible bags secured to the plurality of branch lines, each flexible bag comprising an interior volume and having at least one inlet and outlet and further containing in the interior volume of each plurality of flexible bags a plurality of tablets; and a plurality of pinch valves disposed on the manifold and configured to pinch the main line along one or more locations and the plurality of branch lines secured to the plurality of flexible bags; and wherein the plurality of branch lines comprise an inlet branch line and an outlet branch line for each flexible bag of the plurality of flexible bags and wherein each inlet branch line and each outlet branch line has a respective pinch valve associated therewith.

2. The system of claim 1, wherein the plurality of tablets in at least some of the flexible bags comprises tablets of different composition.

3. The system of claim 1, wherein the plurality of tablets in at least some of the flexible bags comprise one or more of salts, acids, and bases.

4. The system of claim 1, wherein the plurality of tablets in at least some of the flexible bags comprises growth or maintenance media for cells.

5. The system of claim 1, wherein the flexible bags each comprises a fill mark disposed on a surface of the respective flexible bag.

6. The system of claim 1, wherein the flexible bags have been exposed to a sterilizing agent rendering the interior volume of the flexible bags sterile or aseptic.

7. The system of claim 1, wherein each of the flexible bags comprises one or more sealed or sealable openings.

8. The system of claim 1, wherein the flexible bags are vacuum sealed.

9. A method of using the system of claim 1, comprising:

actuating one or more of the plurality of valves to create an inlet flow path from the main line through at least one inlet branch line and into one or more flexible bags; and flowing a pre-determined volume of water into the one or more flexible bags via the main line and the at least one inlet branch line.

10. The method of using the system of claim 9, further comprising removing the one or more flexible bags from the manifold.

11. The method of using the system of claim 9, further comprising simultaneously emptying and diluting the one or more flexible bags by flowing additional water into the one or more flexible bags along the inlet flow path and removing the contents of the one or more flexible bags via the outlet branch line that reconnects to the main line.

* * * * *